(12) United States Patent
Xu et al.

(10) Patent No.: US 12,128,365 B2
(45) Date of Patent: Oct. 29, 2024

(54) METHOD FOR WHOLE BLOOD FILTRATION AND FILTER MEMBRANE STRUCTURE FOR WHOLE BLOOD FILTRATION

(71) Applicant: LANSION BIOTECHNOLOGY CO., LTD, Jiangsu (CN)

(72) Inventors: Xingshang Xu, Jiangsu (CN); Jeffery Chen, Jiangsu (CN); Pei Yu, Jiangsu (CN)

(73) Assignee: LANSION BIOTECHNOLOGY CO., LTD, Jiangsu (CN)

( * ) Notice: Subject to any disclaimer, the term of this patent is extended or adjusted under 35 U.S.C. 154(b) by 707 days.

(21) Appl. No.: 17/059,473

(22) PCT Filed: Apr. 28, 2019

(86) PCT No.: PCT/CN2019/084755
§ 371 (c)(1),
(2) Date: Nov. 30, 2020

(87) PCT Pub. No.: WO2020/220157
PCT Pub. Date: Nov. 5, 2020

(65) Prior Publication Data
US 2021/0205524 A1    Jul. 8, 2021

(30) Foreign Application Priority Data
Apr. 27, 2019    (CN) .......................... 201910346947.0

(51) Int. Cl.
  *B01D 69/12*    (2006.01)
  *A61M 1/36*    (2006.01)
  (Continued)

(52) U.S. Cl.
  CPC .............. *B01D 69/12* (2013.01); *B01D 61/58* (2013.01); *B01D 69/02* (2013.01); *A61M 1/3635* (2014.02);
  (Continued)

(58) Field of Classification Search
  CPC ......... G01N 33/491; G01N 2001/4088; A61M 1/3635; A61M 1/34; B01D 69/02;
  (Continued)

(56) References Cited

U.S. PATENT DOCUMENTS 3,146,163 A * 8/1964 Brewer ............ A61B 5/150412
                                                422/417
6,170,671 B1 * 1/2001 Kitajima ................ B01D 61/20
                                                210/488
(Continued)

FOREIGN PATENT DOCUMENTS

CN    2240724    11/1996
CN    1169886    1/1998
(Continued)

OTHER PUBLICATIONS

"International Search Report (Form PCT/ISA/210) of PCT/CN2019/084755," mailed on Feb. 1, 2020, pp. 1-5.

*Primary Examiner* — Claire A Norris
(74) *Attorney, Agent, or Firm* — JCIP GLOBAL INC.

(57) ABSTRACT

Disclosed are a method for whole blood filtration and a filter membrane structure for whole blood filtration, specifically including the following steps: (1) a filter membrane structure made up of at least two filtration membranes sequentially stacked from top to bottom is selected, and subjected to hemagglutinin treatment for later use; (2) a whole blood sample is added to the filter membrane structure for filtration; and (3) the filtered serum or plasma is collected. The filter membrane structure is composed of at least two
(Continued)

filtration membranes stacked from top to bottom, and the pore sizes of the filtration membranes stacked gradually decrease from top to bottom, and the areas of the same gradually increase or are equal to each other from top to bottom.

8 Claims, 1 Drawing Sheet

(51) Int. Cl.
    *B01D 61/58*     (2006.01)
    *B01D 69/02*     (2006.01)

(52) U.S. Cl.
    CPC .... *B01D 2323/216* (2022.08); *B01D 2325/10* (2013.01); *B01D 2325/36* (2013.01)

(58) Field of Classification Search
    CPC ............... B01D 61/58; B01D 2325/00; B01D 2325/10; B01D 2325/36
    USPC ......................................................... 210/767
    See application file for complete search history.

(56) References Cited

U.S. PATENT DOCUMENTS

| | | |
|---|---|---|
| 2002/0036170 A1 | 3/2002 | Harvey et al. |
| 2006/0188392 A1* | 8/2006 | Tanaka ................ G01N 33/558 |
| | | 422/400 |
| 2014/0263059 A1* | 9/2014 | Burg .................... A61M 1/3635 |
| | | 210/651 |
| 2017/0241977 A1* | 8/2017 | Wilson ................ G01N 33/491 |

FOREIGN PATENT DOCUMENTS

| | | |
|---|---|---|
| CN | 1243251 | 2/2000 |
| CN | 102803958 | 11/2012 |
| CN | 105307758 | 2/2016 |
| CN | 105445083 | 3/2016 |
| CN | 105879936 | 8/2016 |
| CN | 106840828 | 6/2017 |
| CN | 107666961 | 2/2018 |

* cited by examiner

METHOD FOR WHOLE BLOOD FILTRATION AND FILTER MEMBRANE STRUCTURE FOR WHOLE BLOOD FILTRATION

CROSS-REFERENCE TO RELATED APPLICATION

This application is a 371 of international application of PCT application serial no. PCT/CN2019/084755, filed on Apr. 28, 2019, which claims the priority benefit of China application no. 201910346947.0, filed on Apr. 27, 2019. The entirety of each of the above mentioned patent applications is hereby incorporated by reference herein and made a part of this specification.

BACKGROUND

Technical Field

The present invention relates to the technical field of medical detection, and in particular, to a method for whole blood filtration and a filter membrane structure for whole blood filtration.

Description of Related Art

In the prior art, a plasma or serum sample obtained by centrifuging whole blood is generally used to determine the types and concentrations of blood components, for example, metabolites, proteins, lipids, electrolytes, enzymes, antigens, and antibodies. However, centrifugation is laborious and time-consuming, and the subsequent process need to use a pipette to carefully remove the upper layer of serum or plasma, which easily leads to remixing with a small extraction volume. In particular, since centrifugation requires a centrifuge and electricity, it is not suitable for emergency situations and on-site inspections where a small amount of a sample needs to be quickly measured. Therefore, it is necessary to develop an apparatus and method that can efficiently separate serum or plasma from whole blood.

Chinese patent document (application number: 201610200920.7) discloses a microfluidic chip for whole blood filtration and quantitative pipetting, including a chip body, and a whole blood separation mechanism, an anti-backflow microvalve, a liquid quantification mechanism, a propellant mechanism, a flow-blocking microvalve and a liquid outlet mechanism provided on the chip body, where the whole blood separation mechanism includes a liquid inlet, a whole blood filter membrane and a collection unit arranged in sequence to filter and separate blood to obtain plasma, which is transferred to the liquid quantification mechanism under capillary action via the anti-backflow microvalve; the anti-backflow microvalve is used to prevent the plasma in the liquid quantification mechanism from flowing back to the whole blood separation mechanism; the flow-blocking microvalve is used to prevent the plasma from flowing out without external pressure; the propellant mechanism is used to push the quantitative plasma through the flow-blocking microvalve to the liquid outlet mechanism by use of a propellant under pressure; the microfluidic chip for whole blood filtration and quantitative pipetting of this invention can effectively separate blood cells and plasma and quantitatively pipette plasma, and is suitable for use in combination with other types of chips. The disadvantages of this invention are that the blood filtration efficiency of the whole blood filter membrane cannot be guaranteed, clogging is easy to occur, the plasma/serum filtration rate is low, and the application range is narrow, the demand for a large amount of plasma/serum beyond the microfluidic chip cannot be met. In addition, the manufacturing cost of the microfluidic chip is high, and the process is complicated.

Chinese patent document (application number: 201080026906.0) discloses a blood filter and a method for filtering blood. This method includes the following steps: a. providing a blood filter including a filter membrane having opposite first and second sides and a receiving chamber defining a hollow space; and b. injecting a blood sample into the receiving chamber, where the volume of the hollow space is 3 to 20 times larger than the volume of the blood sample, thereby increasing the gas pressure in the receiving chamber, so that the blood sample is filtered by the filter membrane, and the plasma or serum contained in the blood sample is forced to pass through the filter membrane. This invention also relates to a method for filtering blood to produce plasma or serum. The method includes the following steps: a. providing a blood filter including a filter membrane having opposite first and second sides and a receiving chamber having a first volume; b. injecting a blood sample and a gas into a syringe, where the blood sample occupies a second volume in the syringe and the gas occupies a third volume in the syringe; c. connecting the syringe to the blood filter so that they are in fluid communication with each other; and d. increasing the pressure within the syringe until the blood sample is received by the receiving chamber, so that the blood sample is filtered by the filter membrane; wherein the plasma or serum contained in the blood sample is forced to pass through the filter membrane; the sum of the first volume and the third volume is 3 to 20 times larger than the second volume. This invention also relates to a filter membrane having opposite first and second sides; the receiving chamber defines a hollow space for receiving a blood sample to be filtered, and the receiving chamber has at least one opening covered by the filter membrane, where the first side faces the receiving chamber, and the volume of the hollow space of the receiving chamber is 3 to 20 times larger than the volume of the blood sample to be filtered; the sampling chamber is arranged on the second side of the filter membrane. The disadvantages of this invention are that the pressure applied by the user needs to be balanced to reduce the occurrence of erythrecytic hemolysis. If improperly used by the user, excessive pressure will easily cause hemolysis, which may affect the plasma component and thus affect the result accuracy of the test items. Moreover, the use of a syringe with a plunger to add samples can easily cause uneven distribution of blood cell filtration, and the corresponding filter membrane part of the syringe is prone to blockage, which affects filtration efficiency.

Therefore, it is necessary to develop a method for whole blood filtration and a filter membrane structure for whole blood filtration with high whole blood filtration efficiency, convenient operation, reliable quality, low cost, and wide application range.

SUMMARY

The technical problem to be solved by the present invention is to provide a method for whole blood filtration with high whole blood filtration efficiency, convenient operation, reliable quality, low cost, and wide application range, and that can effectively and stably separate plasma/serum from a very small amount of blood, achieving no leakage and hemolysis.

To solve the above technical problem, the technical solution adopted by the present invention is the method for whole blood filtration specifically comprising the following steps:

(1) a filter membrane structure made up of at least two filtration membranes sequentially stacked from top to bottom is selected, and subjected to hemagglutinin treatment for later use;
(2) a whole blood sample is added to the filter membrane structure for filtration; and
(3) a collecting device is set up to collect the filtered serum or plasma.

With the above technical solution, by use of the filter membrane structure composed of at least two filtration membranes being stacked, and by subjecting the filter membrane structure to hemagglutinin treatment, namely, adding hemagglutinin to the filter membrane structure, red blood cells in the whole blood sample can be bound with hemagglutinin in the filter membrane and thus trapped in the filter membrane structure, and white blood cells and other impurities can also be trapped; as a result, it is ensured that red blood cells are completely filtered and adsorbed in the filter membrane structure, so that plasma/serum can be effectively and stably separated from a very small amount of blood, achieving no leakage and hemolysis; where hemagglutinin can be red blood cell antibodies and the like.

A further improvement of the present invention is that the filtration membranes are of porous structure; the pore sizes of the filtration membranes stacked in the filter membrane structure gradually decrease from top to bottom, and the areas of the same gradually increase or are equal to each other from top to bottom. The filter membrane structure includes at least two filtration membranes, and more filtration membranes may also be stacked. The filtration membranes are of porous structure, and the uppermost layer is a loose porous structure, that is, the pore size of the uppermost layer is the largest, and the pore sizes of the stacked filtration membranes in the filter membrane structure gradually decrease from top to bottom. Such a design facilitates layer-by-layer filtration and the passage of plasma or serum, and prevents blood cells and other impurities. The areas of the filtration membranes stacked in the filter membrane structure can be equal to each other from top to bottom, or gradually increase from top to bottom. Such a design facilitates layer-by-layer filtration, and ensures that blood cells and other impurities leaked from the upper layer can further be filtered by the lower layer.

A further improvement of the present invention is that the filter membrane structure comprises two filtration membranes, which are an upper filtration membrane and a lower filtration membrane, respectively, the upper filtration membrane is a hemagglutinin filter membrane, and the lower filtration membrane is composed of at least one hydrophilic microporous membrane; or the upper filtration membrane is a hydrophilic filtration membrane, and the lower filtration membrane is a hemagglutinin filter membrane; hemagglutinin is uniformly distributed in the hemagglutinin filter membrane. Hemagglutinin can be dispersed in the upper filtration membrane or the lower filtration membrane, as long as hemagglutinin is ensured in the filter membrane structure. This can ensure that red blood cells are completely filtered and adsorbed in the filter membrane structure so that red blood cells in the blood are not filtered through.

In a preferred technical solution of the present invention, the upper filtration membrane is a hemagglutinin filter membrane; the lower filtration membrane is a filtration membrane with evenly distributed filter pores and different pore sizes, or the lower filtration membrane is composed of a first lower membrane and a second lower membrane stacked one on another in sequence, and the pore size of the first lower membrane is larger than the pore size of the second lower membrane. Preferably, hemagglutinin is added to the upper filtration membrane, so that red blood cells can agglutinate in the upper filtration membrane, while serum or plasma enters the lower filtration membrane.

In a preferred technical solution of the present invention, the upper filtration membrane is a glass fiber filter paper or nitrocellulose membrane or polysulfone membrane; the lower filtration membrane is a hydrophilic microporous membrane, including glass fiber filter paper or nitrocellulose membrane or polysulfone membrane or cellulose acetate membrane; the filtration in the step (2) is accelerated by upper pressurization or lower suction. The formed filter membrane structure can bear a pressure of 1-30 MPa, which is convenient for actively pressure-pushing the blood to be filtered.

A further improvement of the present invention is that the hemagglutinin filter membrane is obtained by subjecting the filtration membrane to hemagglutinin treatment, and the preparation process thereof is as follows:

1) hemagglutinin is diluted in a hemagglutinin buffer;
2) the filtration membrane is put into the hemagglutinin buffer containing hemagglutinin in step 1) to get wetted, and then air-dried at room temperature, and then placed in an oven at 37° C.-55° C. for more than 2 h; or the filtration membrane wetted in the hemagglutinin buffer is subjected to vacuum drying or freeze-drying treatment.

In a preferred technical solution of the present invention, the hemagglutinin buffer is PB or Tris-HCl or CB; the concentration of the hemagglutinin buffer is 5 mM-1M; the weight of hemagglutinin added to the hemagglutinin filter membrane is not less than 5 ng. PB is sodium phosphate buffer ($NaH_2PO_4$&$Na_2HPO_4$) and potassium phosphate buffer ($K_2HPO_4$&$KH_2PO_4$); Tris-HCl is tris(hydroxymethyl) aminomethane; and CB buffer is carbonate buffer.

A further improvement of the present invention is that the filtration membrane is treated with a buffer before use, and the buffer is any buffer dissolved with BSA or an amino acid, or containing a surfactant component; the treatment process is: after being wetted in the buffer, the filtration membrane is air-dried at room temperature and dried for more than 2 h for later use. Treating each filtration membrane with a buffer can avoid protein adsorption in serum or plasma, and the filtered serum or plasma can be used for other purposes, for example, detection of certain substances therein, etc.

In a preferred technical solution of the present invention, the pore size of the upper filtration membrane is not less than 0.45 μm, and the pore size of the lower filtration membrane is 0.2 μm-4 μm.

In a preferred technical solution of the present invention, the pore size of the upper filtration membrane is 1 μm-5 μm; the thickness of the upper filtration membrane is 0.5 mm-20 mm, and the thickness of the lower filtration membrane is 0.05 mm-2 mm; the weight of hemagglutinin added in the hemagglutinin filter membrane is 20 ng-100 ng. Both the upper filtration membrane and the lower filtration membrane can be a single layer, or can be a multi-layer stack to achieve the required thickness.

A technical problem further to be solved by the present invention is to provide a filter membrane structure for whole blood filtration that can effectively and stably separate plasma/serum from a very small amount of blood.

To address the above technical problem, the technical solution adopted by the present invention is the filter membrane structure for whole blood filtration, composed of at least two filtration membranes stacked in sequence from top to bottom; the filtration membranes are of porous structure; the pore sizes of the filtration membranes stacked in the filter membrane structure gradually decrease from top to bottom, and the areas of the same gradually become larger or are equal to each other from top to bottom. The filter membrane structure includes at least two filtration membranes, and more filtration membranes may also be stacked. The filtration membranes are of porous structure, and the uppermost layer is a loose porous structure, that is, the pore size of the uppermost layer is the largest, and the pore sizes of the stacked filtration membranes in the filter membrane structure gradually decrease from top to bottom. Such a design facilitates layer-by-layer filtration and the passage of plasma or serum, and prevents blood cells and other impurities. The areas of the filtration membranes stacked in the filter membrane structure can be equal to each other from top to bottom, or gradually increase from top to bottom. Such a design facilitates layer-by-layer filtration, and ensures that blood cells and other impurities leaked from the upper layer can further be filtered by the lower layer.

A further improvement of the present invention is that the filter membrane structure comprises two filtration membranes, an upper filter membrane and a lower filter membrane, respectively, the upper filter membrane is a hemagglutinin filter membrane, and the lower filter membrane is composed of at least one hydrophilic microporous membrane; or the upper filter membrane is a hydrophilic filter membrane, and the lower filter membrane is a hemagglutinin filter membrane; hemagglutinin is uniformly distributed in the hemagglutinin filter membrane. Hemagglutinin can be dispersed in the upper filtration membrane or the lower filtration membrane, as long as hemagglutinin is ensured in the filter membrane structure. This can ensure that red blood cells are completely filtered and adsorbed in the filter membrane structure so that red blood cells in the blood are not filtered through.

A further improvement of the present invention is that the upper filtration membrane is a hemagglutinin filter membrane; the lower filtration membrane is a filtration membrane with evenly distributed filter pores and different pore sizes, or the lower filtration membrane is composed of a first lower membrane and a second lower membrane stacked one on another in sequence, and the pore size of the first lower membrane is larger than the pore size of the second lower membrane.

In a preferred technical solution of the present invention, the pore size of the upper filtration membrane is not less than 0.45 μm, and the pore size of the lower filtration membrane is 0.2 μm-4 μm.

In a preferred technical solution of the present invention, the pore size of the upper filtration membrane is 1 μm-5 μm; the thickness of the upper filtration membrane is 0.5 mm-20 mm, and the thickness of the lower filtration membrane is 0.05 mm-2 mm; the weight of hemagglutinin added in the hemagglutinin filter membrane is 20 ng-100 ng.

Compared with the prior art, the beneficial effects of the present invention are that:

(1) by use of the filter membrane structure composed of at least two filtration membranes being stacked, the filtration of serum or plasma in the whole blood and the adsorption of red blood cells and other substances are achieved through the physical structure;

(2) coagulation/anti-coagulation chemicals or antibodies/antigens are added to the filter layer, so that blood cells can agglutinate and be carried in the filter layer, and only serum or plasma can be passed through; hemolysis due to improper pressure control and the resulting influence on the accuracy of the test results are avoided;

(3) regardless of the level of blood cells in the whole blood sample, the method can guarantee blood filtration; according to the size of hematocrit and the volume of whole blood, the filtration output of plasma/serum can be predicted, and on the contrary, quantitative collection of plasma/serum can be realized; a large amount of plasma/serum can be collected by continuously adding whole blood; and (4) the method enables vertical or lateral filtration and has a wide range of applications.

BRIEF DESCRIPTION OF THE DRAWINGS

The following is a further detailed description in conjunction with the accompanying drawings and embodiments of the present invention.

in which: 1—upper filtration membrane; 2—lower filtration membrane; 201—first lower membrane; and 202—second lower membrane.

DESCRIPTION OF THE EMBODIMENTS

Example 1: A filter membrane structure includes two filtration membranes, which are an upper filtration membrane 1 and a lower filtration membrane 2, respectively. The upper filtration membrane 1 is a glass fiber paper with a thickness of 0.5 mm and a pore size of 5 μm. RBC antibody (red blood cell antibody, a hemagglutinin) is dissolved in PB buffer with, and this is used to treat the upper filtration membrane 1 so that the content of RBC antibody in the upper filtration membrane 1 is 100 ng. Then, it is placed in an oven at 37° C.-55° C. to dry for more than 2 h.

The lower filtration membrane 2 is a glass fiber paper with a thickness of 1 mm, and treated with PB buffer dissolved with 1% BSA; and air-dried at room temperature and dried for more than 2 hours.

Figure 1:
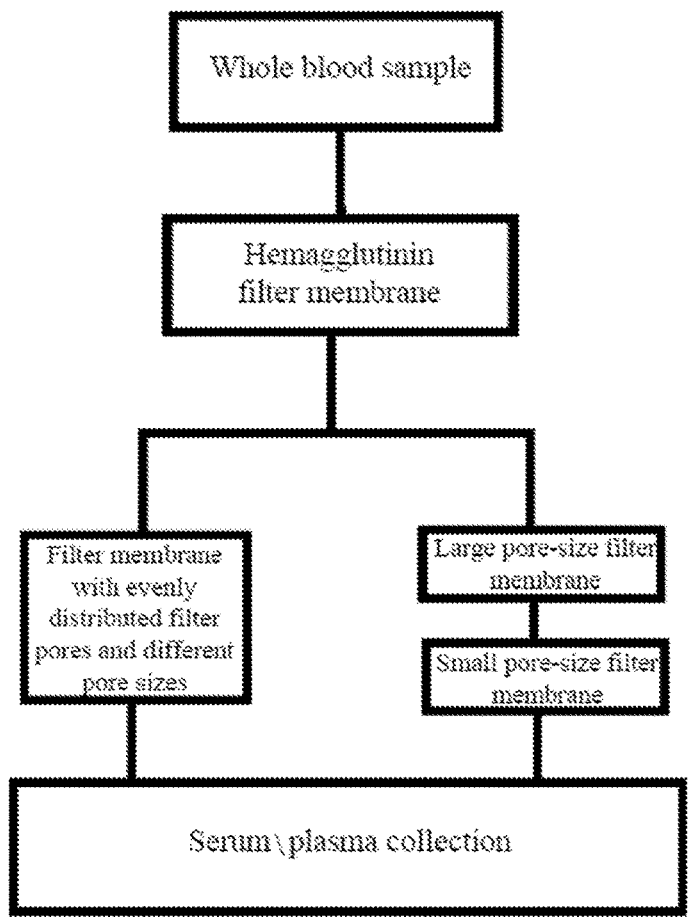
FIG. 1 is a flowchart of a method for whole blood filtration according to the present invention.

As shown in FIG. 1, the method for whole blood filtration specifically includes the following steps:

(1) the above filter membrane structure is selected;

(2) a whole blood sample is added to the filter membrane structure for filtration; the upper pressurization filtration speed is used in the filtration; and (3) a collecting device is set up to collect the filtered serum or plasma.

In the case of active pressure 20 MPa for filtration, the filtration effect can complete the filtration of serum in normal 200 μL whole blood within 30 s, and the filtered serum can reach more than 60 μL.

Examples 2 to 4 all use the filter membrane structure of Example 1 above, and also the same method for whole blood filtration; the difference from Example 1 is the thickness of the upper filtration membrane 1 and the lower filtration membrane 2. The filtration time and the amount of serum collected are shown in Table 1 below.

TABLE 1

Results of whole blood filtration for Examples 1 to 4

| Example | Thickness of upper filtration membrane (mm) | Thickness of lower filtration membrane (mm) | Average filtration time (s) | Volume of serum filtered (μL) | With or without blood cells filtered through |
|---|---|---|---|---|---|
| Example 1 | 0.5 | 1 | 27 | 65 | None |
| Example 2 | 0.25 | 1 | 17 | 70 | Some blood cells |
| Example 3 | 0.5 | 2 | 65 | 50 | None |
| Example 4 | 0.25 | 2 | 60 | 50 | None |

It can be seen form table 1 that Example 1 has achieved the best effect.

Examples 5 to 7 all use the filter membrane structure of Example 1 above, and also the same method for whole blood filtration; the difference from Example 1 is the pressure applied in the filtration in step (2). The filtration conditions are shown in Table 2 below.

TABLE 2

Results of whole blood filtration for Examples 1, 5 to 7

| Example | Air pressure (MPa) | Average filtration time (s) | Volume of serum filtered (μL) | With or without blood cells filtered through |
|---|---|---|---|---|
| Example 1 | 20 | 27 | 65 | None |
| Example 5 | 5 | 62 | 55 | None |
| Example 6 | 10 | 48 | 55 | None |
| Example 7 | 30 | 18 | 65 | Some broken hemolytic red blood cells are filtered through |

It can be seen form table 2 that Example 1 has achieved the best effect.

Examples 8 to 15 all use the whole blood filtration method of Example 1 above, and also the same parameters in the filtration. The filter membrane structure also uses the filter membrane structure of Example 1 above. The difference from Example 1 is the selected materials of the upper filtration membrane 1 and the lower filtration membrane 2 in the filter membrane structure. The filtration conditions are shown in Table 3 below.

TABLE 3

Results of whole blood filtration for Examples 1, 8 to 15

| Example | Upper filtration membrane | Lower filtration membrane | Average filtration time (s) | Volume of serum filtered (μL) | With or without blood cells filtered through |
|---|---|---|---|---|---|
| Example 1 | Glass fiber paper | Glass fiber paper | 27 | 65 | None |
| Example 8 | Glass fiber paper | Polysulfone membrane | 32 | 65 | None |
| Example 9 | Polysulfone membrane | Polysulfone membrane | 35 | 65 | Some blood cells |
| Example 10 | Nitrocellulose membrane | Polysulfone membrane | 48 | 50 | Some blood cells |
| Example 11 | Glass fiber paper | Nitrocellulose membrane | 37 | 60 | None |
| Example 12 | Polysulfone membrane | Nitrocellulose membrane | 38 | 65 | Some blood cells |
| Example 13 | Nitrocellulose membrane | Nitrocellulose membrane | 45 | 65 | Some blood cells |
| Example 14 | Polysulfone membrane | Glass fiber paper | 42 | 60 | Some blood cells |
| Example 15 | Nitrocellulose membrane | Glass fiber paper | 52 | 60 | None |

It can be seen form table 3 that Example 1 has achieved the best effect.

Example 16: Ferric chloride is used as hemagglutinin in this example; taking a 200 μL whole blood sample as an example, when the whole blood sample contains 5000 serum, the structure can filter out no less than 50 μL volume of serum, the amount of serum filtered is more than 50%; the filter membrane structure includes two filtration membranes, which are an upper filtration membrane 1 and a lower filtration membrane 2, respectively. The upper filtration membrane 1 is a glass fiber paper with a thickness of 0.5 mm and a pore size of 5 μm. The upper filtration membrane 1 is treated with a ferric chloride solution with a concentration of 50 mM so that ferric chloride is evenly distributed in the upper filtration membrane 1, and the content of ferric chloride is 100 ng.

The lower filtration membrane 2 is a glass fiber paper with a thickness of 1 mm, and treated with PB buffer dissolved with 1% BSA; and air-dried at room temperature and dried for more than 2 hours.

As shown in FIG. 1, the method for whole blood filtration specifically includes the following steps:

(1) the above filter membrane structure is selected;

(2) a whole blood sample is added to the filter membrane structure for filtration; the upper pressurization filtration speed is used in the filtration; and (3) a collecting device is set up to collect the filtered serum or plasma.

In the case of active pressure 20 MPa for filtration, the filtration effect can complete the filtration of serum in normal 200 μL whole blood within 60 s, and the filtered serum can reach more than 60 μL.

Examples 17 to 19 all use the filter membrane structure of Example 16 above, and the same treatment method of the filter membrane structure and the same method for whole blood filtration; the difference from Example 16 is the thickness of the upper filtration membrane 1 and the lower filtration membrane 2. The filtration time and the amount of serum collected are shown in Table 4 below.

TABLE 4

Results of whole blood filtration for Examples 16 to 19

| Example | Thickness of upper filtration membrane (mm) | Thickness of lower filtration membrane (mm) | Average filtration time (s) | Volume of serum filtered (μL) | With or without blood cells filtered through |
|---|---|---|---|---|---|
| Example 16 | 0.5 | 1 | 58 | 60 | None |
| Example 17 | 0.25 | 1 | 52 | 62 | Some blood cells |
| Example 18 | 0.5 | 2 | 113 | 40 | None |
| Example 19 | 0.25 | 2 | 106 | 42 | None |

It can be seen form table 4 that Example 16 has achieved the best effect.

Examples 20 to 22 all use the filter membrane structure of Example 16 above, and the same treatment method for the filter membrane structure and the same method for whole blood filtration; the difference from Example 16 is the pressure applied on the upper portion in the filtration in step (2). The filtration conditions are shown in Table 5 below.

TABLE 5

Results of whole blood filtration for Examples 16, 20 to 22

| Example | Air pressure (MPa) | Average filtration time (s) | Volume of serum filtered (μL) | With or without blood cells filtered through |
|---|---|---|---|---|
| Example 16 | 20 | 58 | 60 | None |
| Example 20 | 5 | 114 | 45 | None |
| Example 21 | 10 | 87 | 47 | None |
| Example 22 | 30 | 52 | 61 | Some broken hemolytic red blood cells are filtered through |

It can be seen form table 5 that Example 16 has achieved the best effect.

Examples 23 to 30 all use the whole blood filtration method of Example 16 above, and the same parameters in the filtration. The filter membrane structure also uses the filter membrane structure of Example 16 above and is treated with the same treatment method. The difference from Example 16 is the selected materials of the upper filtration membrane 1 and the lower filtration membrane 2 in the filter membrane structure. The filtration conditions are shown in Table 6 below.

TABLE 6

Results of whole blood filtration for Examples 16, 23 to 30

| Example | Upper filtration membrane | Lower filtration membrane | Average filtration time (s) | Volume of serum filtered (μL) | With or without blood cells filtered through |
|---|---|---|---|---|---|
| Example 16 | Glass fiber paper | Glass fiber paper | 58 | 60 | None |
| Example 23 | Glass fiber paper | Polysulfone membrane | 75 | 59 | None |
| Example 24 | Polysulfone membrane | Polysulfone membrane | 76 | 60 | Some blood cells |
| Example 25 | Nitrocellulose membrane | Polysulfone membrane | 94 | 45 | Some blood cells |
| Example 26 | Glass fiber paper | Nitrocellulose membrane | 78 | 55 | None |
| Example 27 | Polysulfone membrane | Nitrocellulose membrane | 81 | 60 | Some blood cells |
| Example 28 | Nitrocellulose membrane | Nitrocellulose membrane | 83 | 58 | Some blood cells |
| Example 29 | Polysulfone membrane | Glass fiber paper | 42 | 60 | Some blood cells |
| Example 30 | Nitrocellulose membrane | Glass fiber paper | 52 | 60 | None |

It can be seen form table 6 that Example 16 has achieved the best effect.

Figure 2:
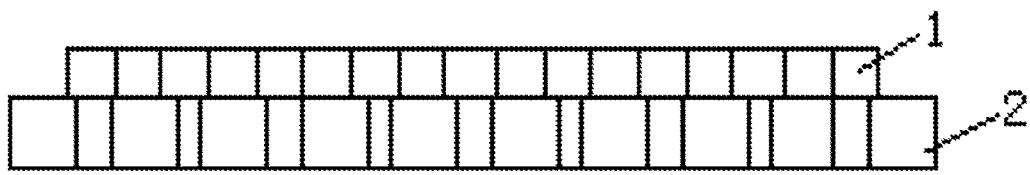
FIG. 2 is a longitudinal cross section of a filter membrane structure for whole blood filtration in Example 31 and Example 33 according to the present invention.

Example 31: As shown in FIG. 2, the filter membrane structure for whole blood filtration is composed of two filtration membranes stacked in sequence from top to bottom; the filtration membranes are of porous structure; the pore sizes of the filtration membranes stacked in the filter membrane structure gradually decrease from top to bottom, and the areas of the same gradually increase from top to bottom; the two filtration membranes included in the filter membrane structure are an upper filtration membrane 1 and a lower filtration membrane 2, respectively, the upper filtration membrane 1 is a hemagglutinin filter membrane, the lower filtration membrane 2 is a filtration membrane with evenly distributed filter pores and different pore sizes; the pore size of the upper filtration membrane 1 is 1 μm, and the pore size of the lower filtration membrane 2 is 0.2-0.5 μm; the thickness of the upper filtration membrane 1 is 0.5 mm, and the thickness of the lower filtration membrane 2 is 1 mm; the hemagglutinin filter membrane is a filtration membrane treated with hemagglutinin, in which hemagglutinin is evenly distributed, and the weight of hemagglutinin is 100 ng.

Figure 3:
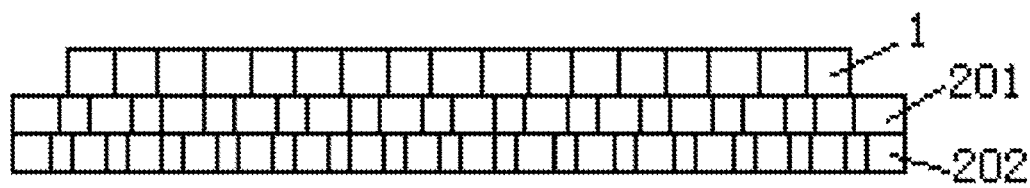
FIG. 3 is a longitudinal cross section of a filter membrane structure for whole blood filtration in Example 32 according to the present invention.

Example 32: As shown in FIG. 3, the difference from Example 31 is that the lower filtration membrane 2 is composed of a first lower membrane 201 and a second lower membrane 202 stacked in sequence from top to bottom, and the first lower membrane 201 has a pore size larger than that of the second lower membrane 202. Specifically: the filter membrane structure for whole blood filtration is composed of two filtration membranes stacked in sequence from top to bottom; the filtration membranes are of porous structure; the pore sizes of the filtration membranes stacked in the filter membrane structure gradually decrease from top to bottom, and the areas of the same gradually increase from top to bottom; the two filtration membranes included in the filter membrane structure are an upper filtration membrane 1 and a lower filtration membrane 2, respectively, the upper filtration membrane 1 is a hemagglutinin filter membrane, and the lower filtration membrane 2 is composed of a first lower membrane 201 and a second lower membrane 202 stacked in sequence from top to bottom, and the pore size of the first lower membrane 201 is larger than that of the second lower membrane 202. The pore size of the first lower membrane 201 is 0.5 μm, and the pore size of the second lower membrane 202 is 0.2 μm; the thickness of the upper filtration membrane 1 is 0.5 mm, and the total thickness of the lower filtration membrane 2 is 1 mm, where the thickness of the first lower membrane 201 is 0.5 mm, and the thickness of the second lower membrane 202 is 0.5 mm.

Example 33: As shown in FIG. 2, the difference from Example 31 is that the upper filtration membrane 1 is a hydrophilic filtration membrane, and the lower filtration membrane 2 is a hemagglutinin filter membrane. Specifically: the filter membrane structure for whole blood filtration is composed of two filtration membranes stacked in sequence from top to bottom; the filtration membranes are of porous structure; the pore sizes of the filtration membranes stacked in the filter membrane structure gradually decreases from top to bottom, and the areas of the same gradually increase from top to bottom; the two filtration membranes included in the filter membrane structure are an upper filtration membrane 1 and a lower filtration membrane 2, respectively, the upper filtration membrane 1 is a hydrophilic filtration membrane, and the lower filtration membrane 2 is hemagglutinin filter membrane; the pore size of the upper filtration membrane 1 is 1 μm, the pore size of the lower filtration membrane 2 is 0.2-0.5 μm; the thickness of the upper filtration membrane 1 is 0.5 mm, and the thickness of the lower filtration membrane 2 is 1 mm; the hemagglutinin filter membrane is a filtration membrane treated with hemagglutinin, in which hemagglutinin is evenly distributed, and the weight of hemagglutinin is 100 ng.

The filter membrane structure includes at least two filtration membranes, and more filtration membranes may also be stacked. The filtration membranes are of porous structure, and the uppermost layer is a loose porous structure, that is, the pore size of the uppermost layer is the largest, and the pore sizes of the stacked filtration membranes in the filter membrane structure gradually decrease from top to bottom. Such a design facilitates layer-by-layer filtration and the passage of plasma or serum, and prevents blood cells and other impurities. The areas of the filtration membranes stacked in the filter membrane structure can be equal to each other from top to bottom, or gradually increase from top to bottom. Such a design facilitates layer-by-layer filtration, and ensures that blood cells and other impurities leaked from the upper layer can further be filtered by the lower layer.

The basic principles, main features and advantages of the present invention have been shown and described above. Those skilled in the art should understand that the present invention is not limited to the foregoing examples. The foregoing examples and the description in the specification are only intended to illustrate the principles of the present invention. Various variations and improvements may further be made to the present invention without departing from the spirit and scope of the present invention. For example, the materials of the filtration membranes or the pore sizes of the same, etc. are changed. Such variations and improvements all fall within the scope claimed by the present invention. The scope claimed by the present invention is defined by the appended claims and their equivalents.

What is claimed is:

1. A method for whole blood filtration, comprising the following steps:

(1) selecting a filter membrane structure made up of two filtration membranes sequentially stacked from top to bottom, and subjecting the filter membrane structure to hemagglutinin treatment;

(2) adding a whole blood sample to the filter membrane structure, and the whole blood sample is filtered by the filter membrane structure to obtain a filtered serum or plasma; and (3) collecting the filtered serum or plasma, wherein the filter membrane structure comprises the two filtration membranes, which are an upper filtration membrane and a lower filtration membrane, respectively, the upper filtration membrane is a hemagglutinin filter membrane, and the lower filtration membrane is composed of at least one hydrophilic microporous membrane; or the upper filtration membrane is a hydrophilic filtration membrane, and the lower filtration membrane is a hemagglutinin filter membrane; hemagglutinin is uniformly distributed in the hemagglutinin filter membrane, wherein the hemagglutinin treatment of the hemagglutinin filter membrane is as follows:

1) diluting hemagglutinin in a hemagglutinin buffer, wherein the hemagglutinin buffer is PB, and PB is sodium phosphate buffer ($NaH_2PO_4$&$Na_2HPO_4$) and potassium phosphate buffer ($K_2HPO_4$&$KH_2PO_4$); and 2) putting the hemagglutinin filter membrane into the hemagglutinin buffer containing hemagglutinin in step 1) to get wetted, air-drying the hemagglutinin filter membrane at room temperature, and then placing the hemagglutinin filter membrane in an oven at 37° C.-55° C. for more than 2 h; or subjecting the hemagglutinin filter membrane wetted in the hemagglutinin buffer to vacuum drying or freeze-drying treatment.

2. The method for whole blood filtration according to claim 1, wherein the filtration membranes are porous structure; pore sizes of the filtration membranes stacked in the filter membrane structure gradually decrease from top to bottom.

3. The method for whole blood filtration according to claim 1, wherein the lower filtration membrane is composed of a first lower membrane and a second lower membrane stacked one on another in sequence, and a pore size of the first lower membrane is larger than a pore size of the second lower membrane.

4. The method for whole blood filtration according to claim 1, wherein the filtration in step (2) is accelerated by upper pressurization or lower suction.

5. The method for whole blood filtration according to claim 1, wherein a concentration of the hemagglutinin buffer is 5 mM-1M; a weight of hemagglutinin added to the hemagglutinin filter membrane is not less than 5 ng.

6. The method for whole blood filtration according to claim 1, wherein the hemagglutinin filter membrane is treated with a buffer, and the buffer is any buffer dissolved with BSA (bovine serum albumin) or an amino acid, or containing a surfactant component; a treatment process is performed, and the treatment process is: after being wetted in the buffer, the hemagglutinin filter membrane is air-dried at room temperature and dried for more than 2 h for later use.

7. The method for whole blood filtration according to claim 1, wherein a pore size of the upper filtration membrane is not less than 0.45 μm, and a pore size of the lower filtration membrane is 0.2 μm-4 μm.

8. The method for whole blood filtration according to claim 7, wherein the pore size of the upper filtration membrane is 1 μm-5 μm; a thickness of the upper filtration membrane is 0.5 mm-20 mm, and a thickness of the lower filtration membrane is 0.05 mm-2 mm; a weight of hemagglutinin added in the hemagglutinin filter membrane is 20 ng-100 ng.

* * * * *